United States Patent [19]
Fisher

[11] Patent Number: 6,132,763
[45] Date of Patent: Oct. 17, 2000

[54] LIPOSOMES

[75] Inventor: Derek Fisher, London, United Kingdom

[73] Assignee: PolyMASC Pharmaceuticals plc, London, United Kingdom

[21] Appl. No.: 08/459,822

[22] Filed: Jun. 2, 1995

Related U.S. Application Data

[63] Continuation of application No. 08/001,900, Jan. 7, 1993, abandoned, which is a continuation of application No. 07/678,955, Apr. 19, 1991, abandoned.

[30] Foreign Application Priority Data

Oct. 20, 1988 [GB] United Kingdom ............... 8824593
Oct. 20, 1998 [WO] WIPO ............... PCT/GB89/01262

[51] Int. Cl.⁷ ............... A61K 9/127; A61K 9/133
[52] U.S. Cl. ............... 424/450; 428/402.2
[58] Field of Search ............... 424/450, 121, 424/9.321, 9.51, 417, 94.3; 436/829; 935/54; 428/402.2

[56] References Cited

U.S. PATENT DOCUMENTS

| | | |
|---|---|---|
| 2,310,679 | 2/1943 | De Groote et al. . |
| 4,016,100 | 4/1977 | Suzuki et al. . |
| 4,320,121 | 3/1982 | Sears . |
| 4,415,665 | 11/1983 | Mosbach et al. . |
| 4,426,330 | 1/1984 | Sears . |
| 4,507,217 | 3/1985 | Sears . |
| 4,534,899 | 8/1985 | Sears ............... 260/403 |
| 4,684,625 | 8/1987 | Eppstein et al. . |
| 4,740,304 | 4/1988 | Tjerneld et al. . |
| 4,904,479 | 2/1990 | Illum . |
| 4,981,692 | 1/1991 | Popescu ............... 424/422 |
| 5,013,556 | 5/1991 | Woodle ............... 424/450 |
| 5,192,548 | 3/1993 | Barenolz et al. . |
| 5,213,804 | 5/1993 | Martin et al. . |
| 5,225,212 | 7/1993 | Martin et al. . |
| 5,349,052 | 9/1994 | Delgado et al. . |
| 5,356,633 | 10/1994 | Woodle et al. . |
| 5,527,528 | 6/1996 | Allen et al. . |
| 5,620,689 | 4/1997 | Allen et al. . |

FOREIGN PATENT DOCUMENTS

| | | |
|---|---|---|
| 0 043 327 | 1/1982 | European Pat. Off. . |
| 0 072 111 | 2/1983 | European Pat. Off. . |
| 0098110 A2 | 1/1984 | European Pat. Off. . |
| 0 118 316 | 9/1984 | European Pat. Off. . |
| 0 140 085 | 5/1985 | European Pat. Off. . |
| 0 144 084 | 6/1985 | European Pat. Off. . |
| 0154316 | 11/1985 | European Pat. Off. . |
| 0 171 946 | 2/1986 | European Pat. Off. . |
| 0 220 797 | 5/1987 | European Pat. Off. . |
| 0 354 855 | 2/1990 | European Pat. Off. . |
| 0572 049 A2 | 1/1993 | European Pat. Off. . |
| 2 552 666 | 9/1984 | France . |
| 59-137409 | 8/1984 | Japan . |
| 2 078 543 | 1/1982 | United Kingdom . |
| 2 079 179 | 1/1982 | United Kingdom . |
| 2 151 203 | 7/1985 | United Kingdom . |
| 2 185 397 | 7/1987 | United Kingdom . |
| 2193631 | 2/1988 | United Kingdom . |
| 89/05824 | 6/1989 | WIPO . |
| 89/06549 | 7/1989 | WIPO . |

OTHER PUBLICATIONS

Roding in Seifen–Ole–Felle–Wachse. 116 p. 509, 1990.
Deamer in Liposomes. Chap. I. pp. 27–51, 1983.
STN File Server (Karlsruhe) Chemical Abstracts, vol. 109, No. 3, (1988) (Colombus, Ohio, U.S.). Hoffman et al., "Transfer of functional insulin receptors to receptor-deficient target cells" (abstract No. 17441m and *Endocrinology* *122* :2865–2872).

(List continued on next page.)

*Primary Examiner*—Gollamudi S. Kishore
*Attorney, Agent, or Firm*—Morrison & Foerster LLP

[57] ABSTRACT

Liposomes with covalently bound PEG moieties on the external surface which demonstrate improved serum half-life following intravenous administration are provided.

11 Claims, 2 Drawing Sheets

OTHER PUBLICATIONS

Unger et al., "Hepatic metastases: liposomal Gd–DTPA–enhanced MR imaging" *Radiology* (1989) 171:81–85.

Szoka, Jr., "Comparative properties and methods of preparation of lipid vesicles (liposomes)" *Ann. Rev. Biophys. Bioeng.* (1980) 9:467–508.

Allen et al., "Gangliosides reduce leakage of aqueous–space markers from liposomes in the presence of human plasma" *Biochem. Biophys. Acta* (1985) 818:205–210.

Ghosh et al., "Grafting of different glycosides on the surface of liposomes and its effect on the tissue distribution of $^{125}$I–labelled y–globulin encapsulated in liposomes" *Biochem. Biophys. Acta* (1980) 632:562–572.

Senior, "Fate and behavior of liposomes in vivo: A review of controlling factors" *CRC Critical Reviews in Therapeutic Drug Carriers* (1987) 3: 123–193.

Tilcock et al., "Liposomal Gd–DTPA: Preparation and characterization of relaxivity" *Radiology* (1989) 171:77–80.

Tilcock et al., "Aqueous two–phase polymer partitioning of lipid vesicles of defined size and composition" *Biochem. Biophys. Acta* (1989) 979:208–214.

Senior et al., "Tissue distribution if liposomes exhibiting long half–lives in the circulation after intravenous injection" *Biochim. Biophys. Acta* (1985) 839:1–8.

Hope et al., "Production of large unilamellar vesicles by a rapid extrusion procedure. Characterization of size distribution, trapped volume and ability to maintain a membrane potential" *Biochim. Biophys. Acta* (1985) 812:55–65.

Hope et al., "Lipid asymmetry induced by transmembrane pH gradients in large unilamellar vesicles" *J. Biol. Chem.* (1987) 262:4360–4366.

Senior et al., "Methodology in assessing liposomal stability in the presence of blood, clearance from the circulation of injected animals, and uptake by tissues" *Liposome Technology* (1984) CRC Press, Chapter 17, 3:263–282.

Budavari et al. *The Merck Index: An Encyclopedia of Chemicals, Drugs, and Biologicals*, Eleventh Edition pg. 1139, Published by Merck & Co., Inc. Rahway, N.J. (1989).

Chaabouni et al., "Affinity Partition of Proteins in Aqueous Two–Phase Systems Containing Polyoxyethylene Glycol–Bound Ligand and Charged Dextrans," Journal of Chromatography, vol. 117:135–143 (1979).

Chemical Abstracts, vol. 109(9), abstract 69845r, Aug. 29, 1988, L. Karr et al., "Cell Separation by immunoaffinity partitioning with polyethylene glycol–modified protein A in aqueous polymer two–phase systems" J. Chromatogr., vol. 442:219–27 (1988).

Chemical Abstracts, vol. 90(21), abstracts 164184, May 21, 1979, A Chaabouni et al., "Affinity partition of proteins in aqueous two–phase systems containing polyoxyethylene glycol–bound ligand and charged dextrans," *J. Chromatogr.*, vol. 171:135–143 (1979).

Cullis et al., "Lipid Polymorphism and the Roles of Lipids in Membranes," Chemistry and Physics of Lipids, vol. 40:127–144 (1986).

Delgado et al., "Coupling of PEG to Proteins by Activation with Tresyl Chloride. Applications in Immunoaffinity Cell Partitioning," in Separations Using Aqueous Phase Systems, editors Fisher, D., and Sutherland, I.A., Plenum Press, New York, pp. 203–210 & 211–213 (1989).

Demiroglou, A. et al., "A Novel Reaction Sequence for the Coupling of Nucleophiles to Agarose with 2,2,2–Trifluoroethanesulfonyl Chloride," Angew. Chem. Int. Ed. Engl., vol. 33(1):120–123 (1994).

Gais, H–J and Ruppert, S., "Modification and Immobilization of Proteins with Polyethylene Glycol Tresylates and Polysaccharide Tresylates: Evidence Suggesting a Revision of the Coupling Mechanism and the Structure of the Polymer–Polymer Linkage," Tetrahedron Letters, vol. 36(22):3837–3838 (1995).

Harris et al., "New Activated PEG Derivatives for Affinity Partitioning," in *Separations Using Aqueous Phase Systems*, editors Fisher, D., and Sutherland, I.A., Plenum Press, New York, pp. 203–210 (1989).

Karr et al., "Cell Separation by Immunoaffinity Partitioning with Polyethylene Glycol–Modified Protein A in Aqueoud Polymer Two–Phase System," Journal of Chromatography, vol. 442:219–227 (1988).

King, J.F. and Gill, M.S., "Reactions of Neopentyl 2,2,2–Trifluoroethanesulfonate (Tresylate) with Nucleophiles: A Model Study for the Coupling of Nucleophiles with Tresyl Agarose," Angew. Chem. Int. Ed. Engl., vol. 34(15):1612–1613 (1995).

March, J. Advanced Organic Chemistry (2nd Edition), McGraw–Hill Kogakusha Ltd., pp. 326–327.

New R., "Introduction," *Liposomes: a practical approach*, Edited by R.R.C. New, Oxford University Press (1990).

Nilsson, K. and Mosbach, K., "Immobilization of Ligands with Organic Sulfonyl Chlorides," Methods in Enzymology, vol. 104:56–69 (1984).

Nilsson, K. and Mosbach, K., "Immobilization of Enzymes and Affinity Ligands to Various Hydroxyl Group Carrying Supports Using Highly Reactive Sulfonyl Chlorides," Biochemical and Biophysical Research Communications, vol. 102(1):449–457 (1981).

Nilsson, K. and Mosbach, K., "Tresyl Chloride–Activated Supports for Enzyme Immobilizations," Methods in Enzymology, vol. 135:65–78 (1987).

Watts et al., "Phospholipid phase transitions as revealed by NMR," Chemistry and Physics of Lipids, vol. 57:195–211 (1991).

LIPOSOMES

This application is a continuation of application Ser. No. 08/001,900, filed Jan. 7, 1993, now abandoned, which is a continuation of application Ser. No. 07/678,955, filed Apr. 19, 1991, now abandoned.

The present invention relates to liposomes bearing polyethylene glycol (PEG) moieties covalently linked to the external surface.

Many ways have been sought to prolong the half life of liposomes in the circulation. Methods have included incorporation of gangliosides in the lipid bilayer, as described by Allen, T. M. et al. *Biochim. Biophys. Acta* 818: 205–210, and coating the liposomal surface with molecules such as glycosides, as described by Ghosh, P. and Bachawat, B. K. *Biochim. Biophys. Acta.* 632: 562–572, and poloxamers, as described by Senior J. *CRC Critical Reviews in Therapeutic Drug Carriers* 3: 123–193 (1987).

There is however, a need for a technique which increases the surface hydrophilicity of liposomes (whether these are small unilamellar vesicles or multilamellar vesicles or large unilamellar vesicles of defined size) while quantitatively retaining aqueous solutes, without crosslinking the vesicles and without conferring on the vesicle a net charge.

A particular problem arises in the use of liposomes to modify the circulation lifetime characteristics of magnetic resonance imaging agents such as Gd-DTPA described by Unger et al., *Radiology,* 171 81–85 (1989) and Tilcock et al., *Radiology,* 171: 77–80 (1989). For use as a perfusion agent it would be desirable to increase the circulation lifetime of liposomal Gd-DTPA.

Once administered i.v., the liposomes are subject to numerous interactions with plasma proteins (eg. HDL) and the Reticulo-endothelial system (RES) which result in destabilisation and clearance of the vesicles from the circulation. Methods that have been employed to date to improve vesicle stability in the circulation have been to incorporate sterols such as cholesterol or glycolipids within the lipid composition of the vesicles. The drawback to both approaches is that it has been shown that the sterol or other high phase transition lipid decreases the permeability of the vesicle membrane to water and so results in a decreased relaxivity for the entrapped Gd-DTPA, thereby decreasing its effectiveness as a contrast agent.

We have surprisingly discovered that the covalent linkage of PEG to the external surface of liposomes can extend the circulation life-time of the liposomes without disrupting the lipid bi-layer.

The present invention therefore provides liposomes having covalently bound PEG moieties on the external surface.

Preferably the PEG moieties are linked to amino groups in the head group of at least one phospholipid species forming the liposome. Suitable phosholipids having amino groups in the head group include phosphatidylethanolamine (PE) and phosphatidyl serine (PS).

The liposomes may be formed of any suitable phospholipid or phospholipid mixture, of which a great many are already known in the literature, provided that at least one of the phospholipid species has a suitable head group for binding PEG. The space within the liposomes may contain any conventional aqueous phase and the liposomes may be presented as an aqueous suspension or as any other conventional formulation, for instance as pharmaceutical formulations also comprising a pharmaceutically acceptable carrier or diluent, for instance as formulations for intravenous administration. Preferred carriers include sterile water for injection with optional accessory ingredients such as buffers, preservatives, antioxidants and isotonic salts.

Preferably the liposomes are large unilamellar vesicles prepared by extrusion (LUVettes), more preferably lipid bilayers consist of a 7:3 to 5:5 molar ratio of dioeylphosphatidyl choline and dioleylphosphatidyl ethanolamine and most preferably the liposomes contain aqueous Gd-DTPA.

The invention further provides a process comprising treating liposomes with a reactive derivative of polyethylene glycol, preferably 2,2,2-trifluoroethanesulphonyl (tresyl) monomethoxy PEG. Tresyl monomethoxy PEG (TMPEG) and its production is described in our co-pending British application no. 8824591.5.

Preferably the reaction between the reactive PEG derivative and the liposomes is conducted in aqueous solution at ambient or physiological temperatures. The reaction occurs at near neutral pH, for instance in physiological buffer but is faster and more extensive at pH9–10. By controlling the ratio of reactive PEG derivative to liposomes, the number of PEG moieties linked to the liposomes may be controlled.

Poly(ethylene glycol) (PEG) is a linear, water-soluble polymer of ethylene oxide repeating units with two terminal hydroxyl groups:

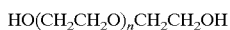

$$HO(CH_2CH_2O)_nCH_2CH_2OH$$

PEG's are classified by their molecular weights, thus PEG 6000, for example, has a molecular weight of about 6000 and n is approximately 135.

PEG's can be covalently linked to proteins by a variety of chemical methods. We have used tresyl chloride (2,2,2-trifluoroethane sulphonyl chloride) to activate the single free hydroxyl group of monomethoxy PEG 5000 (MPEG) but other tresyl halides and other reactive derivatives of MPEG may be used. By having the other hydroxyl group of PEG "blocked" as the unreactive methyl ether, the possibility of producing PEG activated at both ends, which would give rise to cross-linked lipids in the coupling stage, is avoided.

The phospholipids phosphatidylethanolamine (PE) and phosphatidyl serine (PS) have a free amino group in the polar head group. In aqueous solutions phospholipids show lyotropic mesomorphism; most phospholipids adopt closed vesicle structures comprising lipid bilayers (liposomes). PE on its own adopts the $H_{II}$ phase, but in mixtures with phosphatidylcholine (PC) adopts bilayer organizations. We have prepared liposomes from PE/PC mixtures to provide lipid vesicles with the amino groups of PE exposed at both the outer and inner surface. Only the outer PE molecules are accessible to the tresyl-PEG, so the modification is asymmetric.

The amount of PEG linked to the liposome surface can be controlled by varying the lipid composition, the ratio of the reactive derivative of polyethylglycol to the phospholipid having an amino group-containing head group, the duration of the reaction and the pH. The production process may be optimised by systematic studies using, for instance, release of entrapped dye as a marker for disruption of the integrity of the lipid bilayer and by monitoring half-life of treated liposomes in, for instance, the blood stream of mice following intravenous administration.

The major fate of untreated liposomes injected in to the circulation, regardless of size, is uptake by the Kupfer cells of the liver and by fixed macrophages in the spleen. Such uptake by the reticulo-endothelial system (RES) limits the applicability of liposomes in applications such as the formation of reservoirs for the slow release of biologically active molecules and for treatment of tissues other than RES tissues. Treatment of the liposomes according to the present invention, in order to introduce PEG moieties on the external surface surprisingly reduces the interaction between serum and the liposome and surprisingly increases the circulation life-time following intravenous administration.

A particularly preferred use of the PEG-bearing liposomes of the present invention is in the delivery of MR imaging agents such as Gd:diethylenetriaminepentacedic acid chelate.

The invention further provides the use of liposomes having PEG moieties bound to their external surfaces in therapeutic and diagnostic methods practised on the human or animal body, for instance as delivery means for drugs and for contrast agents for Magnetic resonance (MR) imaging. The invention provides a therapeutic or diagnostic process comprising intravenous administration of an effective, non toxic amount of a PEG-bearing liposomes as hereinbefore described containing a diagnostic or therapeutic agent to a human or non-human animal in need thereof.

BRIEF DESCRIPTION OF THE DRAWINGS

The invention will now be illustrated by the figures of the accompanying drawings which.

Figure 1A:
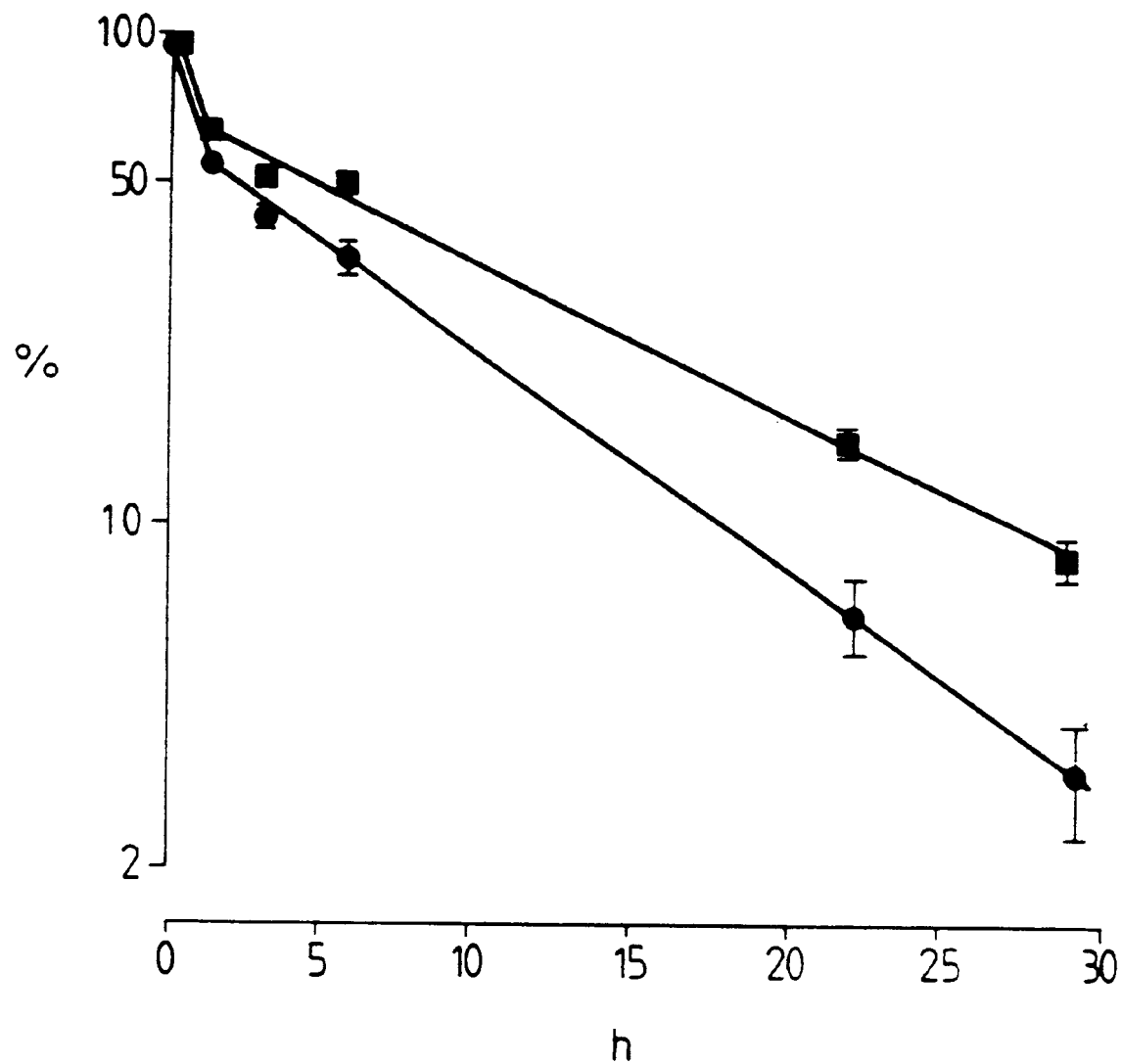
FIG. 1A: SUVs of composition DSPC:PE:Cholesterol (molar ratio 0.4:0.1.5) either PEGylated ( ) or untreated ( ) were injected iv into mice (0.4 mg/25 g mouse). Blood levels of CF (dose±se, 5 animals) are shown; $^3$H phospholipid clearance was similar (not shown).

The invention will now be illustrated by the following Examples:

EXAMPLES 1–10

PREPARATION OF PEGYLATED LIPID VESICLES

A. Preparation of Activated Tresyl-MPEG

Tresylated monomethoxy PEG (TMPEG) was obtained by treating dry monomethoxy PEG 5000, which is available from Union Carbide, in dichloromethane, with tresyl chloride (2,2,2-trifluoroethane-sulphonyl chloride) which is available from Fluka, at room temperature, using pyridine as a base catalyst. Dichloromethane was removed under reduced pressure and the solid obtained dissolved in methanol-HCl mixture (0.3 ml conc HCl per 1000 ml) and reprecipitated at between −20 and 0°. The solid was isolated by centrifugation, the process repeated until the sample was free of pyridine (detected at 255 nm), and then the solid was reprecipitated from methanol until acid free.

B. PEGylation of Lipid Vesicle Surfaces

The resulting TMPEG was reacted with lipid vesicles at room temperature in buffered solutions (see below). The MPEG covalent attachment of the MPEG to the outer surface of the vesicles was demonstrated by the alteration in the partitioning behaviour of the vesicles in aqueous two-phase systems of PEG and dextran, by a method similar to that of Tilcock et al., *Biochim. Biophys. Acta* 979:208–214 (1989). The composition of the phase system was adjusted so that the vesicles showed a low partition in the top PEG-rich phase; vesicles were at the interface or in the MPEG bottom dextran-rich phase. Attachment of MPEG to the vesicle surface makes them more "PEG-like" (increases their wetting by the PEG-rich phase) and they partition to the top phase.

Example 1

PEGylation of MLVs (Multilamellar Vesicles)

Multilamellar vesicles containing 20% (w/w) egg phosphatidylethanolamine (EPE) and 80% (w/w) egg phosphatidylcholine (EPE) and $^{14}$C EPC were prepared in 0.125M NaCl containing 0.05M sodium phosphate buffer, pH 7.5 (PBS) at 10 mg total lipid/ml. 0.1 ml samples of vesicles were incubated with solutions of TMPEG prepared in PBS (final concentrations 0–170 mg/ml) for 2 hours at room temperature. Samples were partitioned by adding samples (0.05 ml) to a biphasic system (1 ml of top phase and 1 ml of bottom phase of a phase system of 5% (w/w) PEG 6000 and 5% (w/w) Dextran T500 in 0.15M NaCl containing 0.01M sodium phosphate, pH 6.8, mixing the systems and measuring the radioactivity in samples taken from the mixture immediately after mixing (total) and from the top and bottom phases after phase separation was completed (20 min).

The results in Table 1 show that exposure of the liposome to TMPEG increases their partition into the PEG-rich top phase. This indicates that PEG has become attached to the liposome, presumably by the covalent attachment to the amino group of the EPE.

TABLE 1

The effect of TMPEG on the partitioning behaviour of multilamellar vesicles of EPE/EPC (2:8)

| FINAL TMPEG | PARTITION (%) | | | n |
|---|---|---|---|---|
| (mg/ml) | Top Phase | Interface | Bottom | Phase |
| 0.0 | 9.1 ± 4.7 | 84.5 ± 4.1 | 6.4 ± 2.4 | 9 |
| 2.0 | 14.5 ± 5.4 | 80.2 ± 4.2 | 5.3 ± 1.6 | 3 |
| 8.0 | 44.9 ± 6.3 | 50.8 ± 6.5 | 4.3 ± 0.4 | 3 |
| 12.5 | 74.7 ± 9.5 | 20.1 ± 10.5 | 5.2 ± 1.4 | 3 |
| 25.0 | 96.3 ± 7.8 | 3.1 ± 3.6 | 4.6 ± 0.8 | 4 |
| 50.0 | 89.3 | | 6.5 | 4.5 | 1 |
| 100.0 | 88.8 | | 5.1 | 6.1 | 1 |
| 170.00 | 89.3 | | 6.5 | 4.2 | 1 |

The presence of PE in the vesicle is required for TMPEG to have any effect. When MLVs of 100% EPC were treated with TMPEG for two hours and then partitioned in a 5%/5% PEG 6000-Dextran T500 systems in 0.15M NaCl buffered with 0.01M sodium phosphate, pH 6.8 there was no difference compared to MLVs treated with buffer (Table 2).

TABLE 2

Effect of TMPEG on eggPC Multilamellar vesicles

| FINAL TMPEG | PARTITION (%) | | | n |
|---|---|---|---|---|
| (mg/ml) | Top Phase | Interface | Bottom | Phase |
| 0 | 22.5 ± 13.0 | 71.6 ± 12.0 | 5.9 ± 1.0 | 5 |
| 25 | 25.8 ± 13.0 | 67.8 ± 14.0 | 6.4 ± 1.0 | 5 |

The activity of TMPEG declines on storage. Samples that had lost their ability to PEGylate proteins were found to have no effect on the partitioning of liposomes containing EPE. This observation, taken together with the inablity of TMPEG to effect non-PE containing vesicles supports the conclusion that TMPEG attaches to PE specifically, and that altered partitioning does not arise from adsorption of TMPEG to vesicle surfaces.

Example 2

PEGylation of SUVs (Small Unilamellar Vesicles)

SUVs composed of distearoylphosphatidylcholine (DSPC), dipalmitoylphosphatidylethanolamine (DPPE) and cholesterol in molar ratio 0.8:0.2:1 were prepared by the method of Senior et al., *Biochim. Biophys. Acta.* 839: 1–8 (1985), with tracer $^3$H-DPPC ($6\times10^6$ dpm per 30 mg phospholipid): 25 mg DSPC, 5.5 mg DPPE and 15 mg cholesterol were hydrated in 2 ml PBS (0.125M NaCl buffered with 0.05M Naphosphate buffer, pH 8.5). To measure liposomal retention of water-soluble molecules during the coupling reaction and subsequent procedures, Carboxy-fluorescein was partially purified and entrapped at 0.15M as described by Senior et al., *Biochim. Biophys. Acta* 839: 1–8 (1985). 0.5 ml SUV were incubated with an equal volume of TMPEG, prepared in PBS (0.125M NaCl buffered with 0.05M Naphosphate buffer, pH 8.5) at 125 mg/ml. for 2 hours at room temperature (Ratio of TMPEG to total DPPE is 6.25). The vesicles were then separated from unreacted TMPEG by gel filtration on Sepharose 4B-CL and partitioned as in Example 1 in a phase system of 5% PEG 8000 (Union Carbide) and 5% Dextran T500 (Pharmacia) in 0.15M NaCl containing 0.01M sodium phosphate, pH 6.8. The results in Table 3 show that exposure of the liposomes to TMPEG increases their partition into the PEG-rich top phase compared with vesicles treated only with buffer (control). This suggests that PEF has been covalently linked to the amino group of the DPPE. PEGylation proceeded without the loss of the entrapped CF.

TABLE 3

Phase Partitioning of PEGylated and unPEGylated SUVs

| VESICLES | PARTITION[1] (%) | | |
|---|---|---|---|
| Phase | Top Phase | Interface | Bottom |
| Untreated | 1.4 ± 0.2 | 36.0 ± 5.0 | 62.5 ± 5.1 |
| TMPEG-treated | 96.5 ± 1.0 | 1.4 ± 1.1 | 2.1 ± 0.4 |

[1]mean ± n = 6

Example 3

The SUVs, as used in Example 2, were treated with TMPEG (125 mg/ml) and their partitioning compared with SUVs treated with MPEG (125 mg/ml) or buffer: the TMPEG treated vesicles were completely (100%) partitioned into the top phase, whereas the MPEG-treated vesicles and buffer-treated vesicles showed no top phase partitioning, and similar even distributions between the interface and the bottom phase. This provides additional support for the suggestion that TMPEG acts by covalent attachment to the vesicle surface, and not by adsorption.

Example 4

PEGylation of LUVettes (Large Unilamellar Vesicles Prepared by Extrusion) of Defined Size LUVettes were prepared as described by Tilcock et al., *Biochim. Biophys. Acta* 979:208–214 (1989).

LUVettes of 100 nm diameter were prepared at a final concentration of 10 mg/ml. Mixtures of dioleylphosphatidylcholine (DOPC) and dioleylphosphatidyl ethanolamine (DOPE) in chloroform at various molar ratios (total 20 mmoles) were combined with 2uC of $^3$H DPPC and the solvent removed by evaporation under reduced pressure (<0.1 mn Hg) for 2 hours. The lipid was dispersed by vortex mixing at room temperature in 1.55 ml of 50 mM Hepes, 100 mM NaCl pH 7–9 to give a final lipid concentration of 10 mg/ml. Large unilamellar vesicles were then produced by repeated extrusion (10 times) of the lipid dispersion MLVs through two stacked 100 nm polycarbonate filters using the Extruder device (Lipex Biomembranes, Canada) by the method of Hope et al., *Biochim. Biophys. Acta* 812: 55–65 (1985). Diameters determined by QEL using a Nicomp model 270 particle analyzer.

The vesicles were PEGylated by incubation with 40 ul of buffer containing TMPEG at room temperature. At intervals 20 ul samples were removed and partitioned in a phase system of 1.5 ml top phase and 1.5 ml bottom phase of a 5% PEG 8000 (Union Carbide) and 5% Dextran T500 (Pharmacia) system prepared 0.15M NaCl buffered with sodium phosphate pH 6.8 at room temperature. Samples of top and bottom phase were removed for counting 20 min after the phase had been mixed and allowed to separate. This phase system was selected so that the partitioning of the untreated vesicles into the top phase was extremely low (>5%); the majority of the vesicles were approximately equally divided between the bottom phase and the bulk interface.

Example 5

The time course and pH dependency of the PEGylation reaction using a two-fold excess of TMPEG to the DOPE present at the outer surface of LUVettes are used in Example 4. At pH 8–9 incubation with TMPEG rapidly caused a time dependent transfer of vesicles to the top phase. At pH 7.5 the reaction was considerably slower and at pH 7.0 there was virtually no transfer to the top phase. In a separate experiment in which the bottom phase and interface partitioning was also measured it is seen that at pH 7.2, although top phase partitioning does not alter there was decrease in bottom phase partitioning with an increase in interface partitioning, indicating that PEGylation proceed at pH 7.2 albeit more slowly than at higher pHs. At pH 8 the partitioning moves from the bottom phase to the interface and then to the top phase; at pH 9 and 10 vesicles are moved rapidly from the interface and bottom phase to the top phase. Thus the PEGylation reaction is very sensitive to pH and appropriate choice of conditions of time and pH can determine the degree of PEGylation. The extent of PEGylation can also be controlled by the amount of TMPEG used. Treating 100 nm Luvettes of DOPE/DOPC (0.2:0.8) at pH 9.0 with varying molar ratios of TMPEG increased partitioning into the top phase consistent with increasing PEGylation. There was a marked increase in top phase partitioning between the molar ratios 1.0 and 1.3 from 20% to 90%. When the partitioning in the bottom phase and at the interface is also measured (Table 4) it can be seen that PEGylation at the lower ratios of TMPEG:outerDOPE molar ratio causes a progressive change in the partition from the bottom phase to the interface and subsequently to the top phase demonstrating gradations in the degree of PEGylation.

It is clear from the time course of the partitioning that reaction at pH 9 is virtually complete by 1 hour. Thus defined degrees of PEGylation are obtained by control of the TMPEG:DOPE ratio.

TABLE 4

| Molar ratio TMPEG: DOPE at outer surface | Partitioning (%) | | |
|---|---|---|---|
| | Bottom | Interface | Top |
| 0 | 50 | 40 | 10 |
| 0.2 | 56 | 41 | 3 |
| 1.0 | 28 | 58 | 13 |
| 1.3 | 1 | 9 | 89 |

Measurement of the fraction of amino groups (from PE) exposed at the outer surface of the LUVettes, made by the method of Hope, M. J. and Cullis. P. R. *J. Biol. Chem.* 262: 4360–4366 (1987) in 0.05M TNBS in borate buffer at pH 8.5, gave values of 47% for DOPC:DOPE vesicles (8:2), close to the theoretical value of 50% for equal distribution of the PE between the inner and outer surfaces. PEGylation caused a decrease in the PE content detectable by this assay, suggesting covalent attachment of the MPEG to the free $NH_2$ group of PE. For example, when a 3-fold mole excess of TMPEG to outer PE was added to DOPC:DOPE vesicles of 7:3 molar ratio for 1 hour, the percentage of outer PE PEGylated was 36%; when a 6-fold molar excess was added, this percentage PEGylation increased to 45%.

Example 6

Stability of Lipid Vesicles to PEGylation

The stability of lipid vesicles was measured by the extent of efflux of 6CF (6-carboxyfluorescein) as described by Senior and Gregoriadis in "Liposome Technology." (G Gregoriadis ed) vol 3, p. 263 (1984) CRC Press. LUVettes of 100 nm composed of DOPC:DOPE were prepared with entrapped 50mM 6CF (6-carboxyfluorescein) in 100 mM NaCl at pH 8.5, external 6CF was removed by column chromatography on Sephadex G-25 using 50 mM Hepes, 100 mM NaCl, pH 8.5 as eluant. Samples for latency measurement were added to 4 ml of buffer (100 mM NaCl, 50 mM HEPES pH 9) and fluorescence measured (dye released), and to 4 ml of buffer containing 25 mM octylglucoside, incubated for 30 mon at 37° to ensure complete disruption of the vesicles and fluorescence measured (total dye). Fluorescence was measured at 490 nm excitation and 520 nm emission.

LUVettes of 100 nm were PEGylated with TMPEG without any loss of latency. Vesicles of DOPC: DOPE 8:2 were treated with a 3 fold molar ratio of TMPEG to DOPE present in the outer vesicle surface at pH 8.5 to ensure extensive PEGylation (demonstrated by phase partitioning). There was no leakage of 6CF out of the vesicles over a period of 2 hours demonstrating that PEGylation occurs without disruption of the lipid bilayer.

Example 7

Interaction of SUVs With Serum 0.1 ml of SUVs of composition DSPC:PE:Cholesterol (molar ratio 0.4:0.1:0.5), with or without coupled PEG (see above) were incubated at 376° with 0.5 ml of fresh plasma (mouse) or buffer. Samples were removed at intervals and partitioned as in Example 2 above. SUVs partitioned about 20% top phase, 60% interface and 20% bottom phase. Treatment with serum caused an immediate (within 1 min) alteration in the vesicle surface properties indicated by their partition: 0% top phase, 40% interface and 60% bottom phase. The plasma proteins alone partitioned mainly to the bottom phase (68% bottom, 32% top; Partition coefficient= 0.47±0.02, n=4). Thus it appears that the SUVs are immediately coated with serum proteins which then cause the vesicles to partition with similar characteristics to the proteins. PEGylation of the SUVs increased their partition into the top phase (almost 100%); on exposure to serum there was a change in their partition towards the interface and the bottom phase, but importantly this process was very slow compared with the virtually instantaneous effect of serum on unPEGylated SUVs. Since the partitioning behaviour relates to the sum of the forces imposed by the PEGylation and serum binding, and with the former is not a linear function, it is not simple to determine whether the effect of serum on partition is equal for the PEGylated and for the unPEGylated liposomes. This could, however, be determined with a detailed dose response analysis of the effect of PEGylation on the partition coefficient so that the influence of serum could be determined at various parts of the dose response curve in "PEG-equivalents". This would establish whether serum had different effects on the PEGylated and unPEGylated liposomes. The order of magnitude differences in partition behaviour suggests that PEGylation slows down the adsorption of serum components onto the vesicles.

Separation of the SUVs exposed to serum by gel chromatography gave vesicles which showed partitioning behaviour close to that of the vesicles before exposure. Thus the interaction between vesicles and serum is reversed by reisolation of the vesicles.

These experiments also demonstrate that the altered surface properties of the SUVs imposed by PEGyliition are not substantially reversed by serum protein adsorption.

Example 8

Stability of LUVettes to Serum is Increased by PEGylation

To determine the stability of LUVettes to serum vesicles containing entrapped 6CF (50 ul) were incubated at 37° with 0.5 ml serum (freshly hydrated lyophilised human serum, Monitrol-ES, Dade Diagnostics) to provide a final lipid concentration of approx 1 mg/ml, a concentration corresponding to the maximum in vivo serum concentrations expected on the basis of the imaging experiments of Unger et al Radiology 171: 81–85. Samples were removed at intervals and the 6CF released was measured fluorimetrically. Vesicles were PEGYlated with a 3-fold excess of TMPEG to outer surface DOPE overnight at room temperature, after which time there had been loss of latency.

50 nm vesicles of DOPC:DOPE at 8:2 molar ratio showed considerable loss of latency in the presence of serum (eg only 10% latency remained after 2 hrs) which PeGylation did not decrease; 100 nm vesicles showed a latency of 35% after 2 hrs which was unaffected by PEGylation; 200 nm vesicles showed a smaller loss of latency (eg 65% latency remained after 2 hrs), which also was not inhibited by PEGylation. However, for 100 nm vesicles of 7:3 molar ratio DOPC:DOPE, PEGylation decreased serum induced loss of latency by a factor of 2. Increasing the DOPE content to 40 mole % and 50 mole % increased the stability of the vesicles to serum; nevertheless PEGylation produced additional stabilisation. Table 5 summarises these data.

TABLE 5

Stabilisation of 100 nm LUVette latency to serum (2hr, 37°) by PEGylation

| DOPC:DOPE molar ratio | Latency (%) UnPEGYLATED | PEGylated |
|---|---|---|
| 8:2 | 35 | 35 |
| 7:3 | 55 | 83 |
| 6:4 | 90 | 95 |
| 5:5 | 92 | 99 |

Example 9

PEGylation Does not Alter the Relativity of Encapsulated Gd-DTPA

Gd-DTPA was encapsulated in LUVettes composed of DOPC:DOPE 7:3 by the method of Tilcock et al *Radiology* 171: 77–80 (1989).

Half of the sample was PEGylated with TMPEG (molar ratio of TMPEG: PE on outer surface of 3:1). Both control and PEGylated samples were diluted in saline bilffer (139 mM NaCl, 10 m Hepes, 6 mM KCl, pH 8.5) to give four samples with effective Gd concentrations of 2, 1, 0.5, and 0.25 mM (calculated as described by Tilcock et al., Radiology 171: 77–80 (1989) given the known trap volume of the vesicles, the lipid concentration and assuming the concentration of entrapped Gd-DTPA was 0.67M. ) Samples of 10–12 ml were imaged with a Toshiba 0.5T MRT-50A whole body scanner. Relaxivites are obtained from linear regressions of 1/T1 (spin lattice relaxation time constant) against the effective Gd-DTPA concentration. These were unaffected by PEGylation of the vesicles.

Example 10

PEGylation of SUVs Decreases Their In Vivo Clearance

SUVs of composition DSPC:PE:Cholesterol (molar ratio 0.4:0.1:0.4) (0.2 ml containing 0.4 mg phosphpholipid) were injected intravenously into the tail vein of male TO mice (5 in each group). Clearance of PEGylated and unPEGylated vesicles was assessed from entrapped CF and $^3$H-radiolabelled phospholipid measured in blood samples (25 ul) withdrawn at intervals in the method of Senior and Gregoriadis in "Liposome Technology" vol 3 pp 263–282 (1984), CRC Press. In another experiment an 0.8 mg dose of phospholipid was given as the supernatant from ultracentrifugation at 100,000 g for 1 hour, which contains small vesicles of 20–100 nm (average 50 nm) as described by Senior et al Biochim Biophys Acta 839: 1–8 (1985).

Figure 1B:
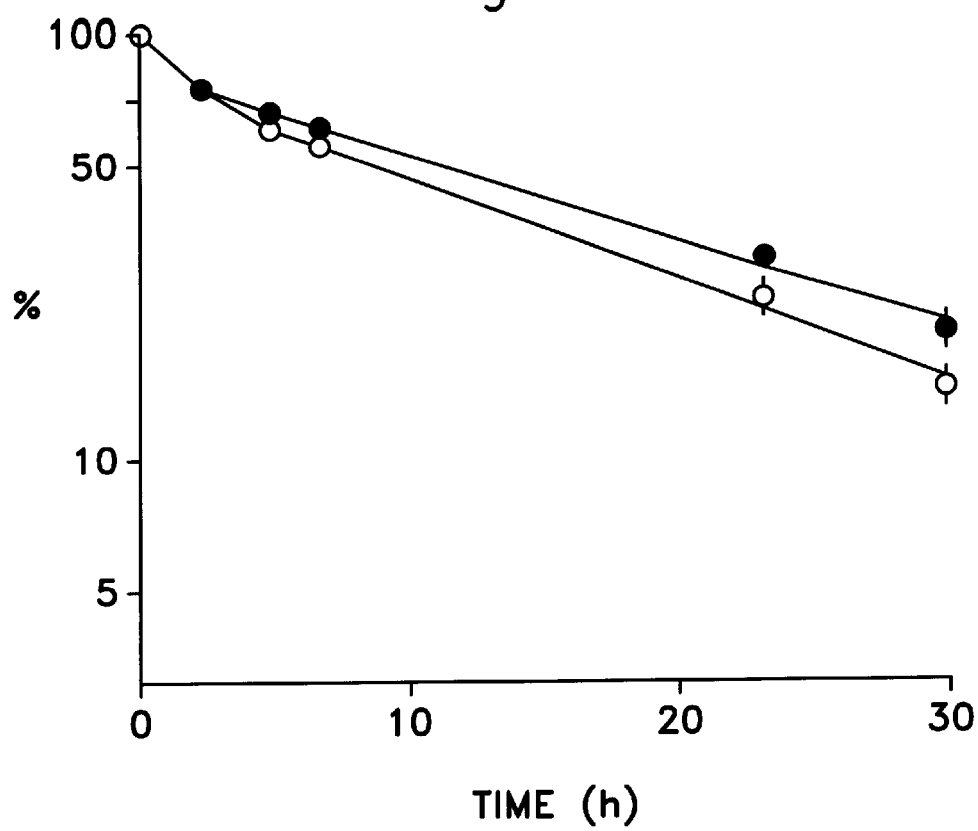
FIGS. 1B: and 1C: Identical conditions to FIG. 1A except that the SUV preparation had been centrifuged to 100,000 g for 1 hr to remove larger vesicles and the injected dose was 0.8 mg/25 g mouse. Both CF FIG. 1B clearance and $^3$H phospholipid clearance FIG. 1C are shown for PEGylated ( ) and unPEGylated ( ) vesicles.
Figure 1C:
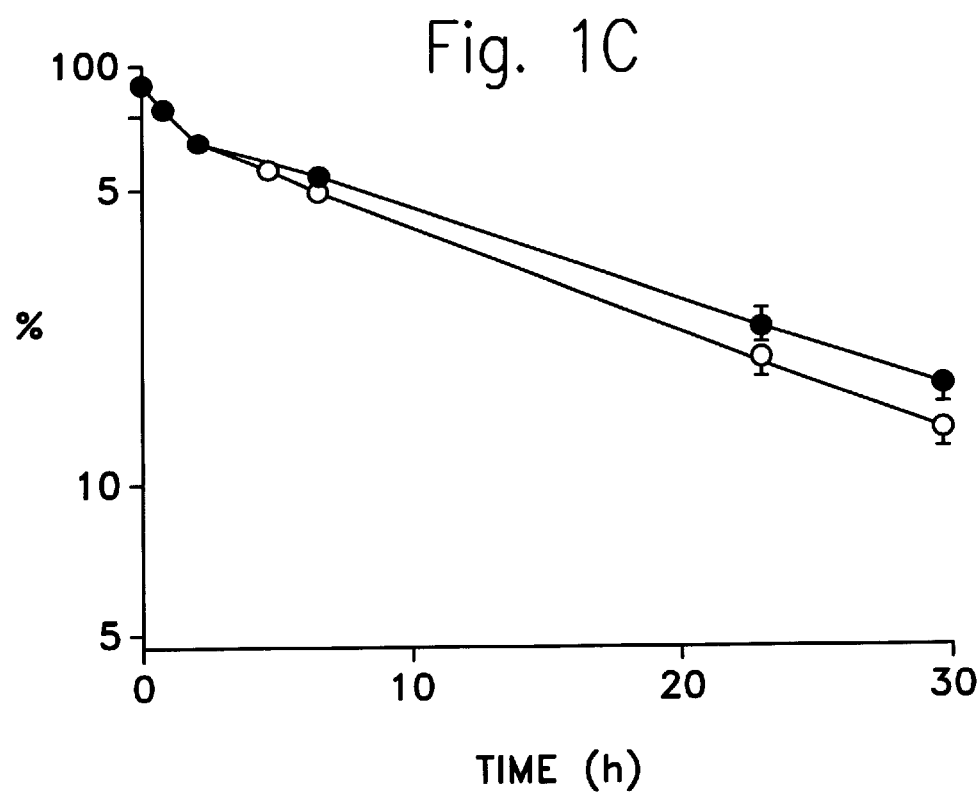
FIG. 1. shows a comparison of the clearance of PEGylated SUV's and unPEGylated SUVs from the circulation in mice.

FIG. 1A shows the clearance of SUVs after intravenous administration of a sonicated, uncentrifuged preparation. This preparation contains, presumably, some larger vesicles which are cleared rapidly, in both the PEGylated and unPEGylated samples. However the slower clearance phase corresponds to about 50–60% of the lipid dose and showed a marked difference in the half life of the PEGylated sample (10 hr) compared with the unPEGylated preparation (7 hr). In the preparation in which the larger vesicle had been removed (FIG. 1B and FIG. 1C) the PEGylated vesicles had half life of 14 hr compared with untreated vesicles of 12 hr.

What is claimed is:

1. Liposomes having PEG moieties covalently bound to phospholipids on the external surface, wherein said liposomes are selected from large unilamellar vesicles (LUV's), small unilamellar vesicles (SUV's) and multilamellar vesicles (MLV's).

2. Liposomes according to claim 1, wherein said liposomes comprise a mixture of lipids.

3. Liposomes according to claim 2 wherein the lipid bilayers comprise a 7:3 to 5:5 molar ratio of DOPC to DOPE.

4. Liposomes according to claim 2 wherein the lipid bilayers comprise a mixture of dioleylphosphatidylcholine (DOPC) and dioleylphosphatidylethanolamine (DOPE).

5. A pharmaceutical composition comprising an aqueous suspension of liposomes according to claim 1 and a pharmaceutically acceptable carrier or diluent.

6. A process for producing a liposome according to claim 1 comprising treating liposomes with a polyethylene glycol having at least one activating group capable of coupling said polyethylene glycol to said liposome.

7. A process according to claim 6 wherein the reactive derivatave is 2,2,2-trifluoroethane sulphonyl-monomethoxy-polyethylene glycol.

8. Liposomes according to claim 1, obtained by reacting 2,2,2-trifluoroethane sulfonyl-monomethoxy PEG derivatives with liposomes.

9. Liposomes according to claim 1, wherein essentially all said PEG moieties are bound on the external surface of the liposome.

10. Liposomes according to claim 1, wherein said liposomes display an enhanced partition to the PEG-rich (upper) phase of a PEG:dextran aqueous two phase system in which liposomes not having PEG moieties covalently bound to phospholipids on the external surface separate predominantly to the interface or bottom phase.

11. Liposomes according to claim 1, wherein said liposomes display a decreased adsorption of serum proteins than liposomes not having PEG moities covalently bound to phospholipids on the external surface.

* * * * *

UNITED STATES PATENT AND TRADEMARK OFFICE
CERTIFICATE OF CORRECTION

PATENT NO.   : 6,132,763
DATED        : October 17, 2000
INVENTOR(S)  : Derek Fisher It is certified that error appears in the above-identified patent and that said Letters Patent is hereby corrected as shown below:

<u>Title page,</u>
Item [30], Foreign Application Priority Data, correct the filing date for "PCT/GB89/01262" from "1998" to -- 1989 --.

Signed and Sealed this

Twenty-first Day of January, 2003

JAMES E. ROGAN
*Director of the United States Patent and Trademark Office*